US007030089B2

(12) United States Patent
Geroni et al.

(10) Patent No.: US 7,030,089 B2
(45) Date of Patent: Apr. 18, 2006

(54) USE OF SUBSTITUTED ACRYLOYL DISTAMYCIN DERIVATIVES IN THE TREATMENT OF TUMORS ASSOCIATED WITH HIGH LEVELS OF GLUTATHIONE

(75) Inventors: Maria Cristina Geroni, Milan (IT); Paolo Cozzi, Milan (IT); Italo Beria, Milan (IT)

(73) Assignee: Pharmacia Italia S.p.A., Milan (IT)

( * ) Notice: Subject to any disclaimer, the term of this patent is extended or adjusted under 35 U.S.C. 154(b) by 0 days.

(21) Appl. No.: 10/258,620

(22) PCT Filed: Apr. 19, 2001

(86) PCT No.: PCT/EP01/04470

§ 371 (c)(1),
(2), (4) Date: Nov. 7, 2002

(87) PCT Pub. No.: WO01/85144

PCT Pub. Date: Nov. 15, 2001

(65) Prior Publication Data

US 2003/0207794 A1    Nov. 6, 2003

(30) Foreign Application Priority Data

May 8, 2000     (GB) .................................. 0011059

(51) Int. Cl.
*A61K 31/4025* (2006.01)
(52) U.S. Cl. .......................................... 514/17; 514/18
(58) Field of Classification Search ................ 530/329, 530/330, 331, 332; 514/17, 18
See application file for complete search history.

(56) References Cited

U.S. PATENT DOCUMENTS

| 5,646,177 A | 7/1997 | Koch et al. .................. 514/452 |
| 5,880,097 A | 3/1999 | Lyttle et al. .................. 514/18 |

FOREIGN PATENT DOCUMENTS

| EP | 0 246 868 | 11/1987 |
| EP | 0 265 719 | 5/1988 |
| EP | 0 388 948 | 9/1990 |
| EP | 0 420 121 | 4/1991 |
| GB | 2 178 036 | 2/1987 |
| WO | WO 90 11277 A | 10/1990 |
| WO | WO 96 05196 A | 2/1996 |
| WO | WO 97 28123 | 8/1997 |
| WO | WO 97 43258 | 11/1997 |
| WO | WO 98 04524 A | 2/1998 |
| WO | WO 98 21202 A | 5/1998 |
| WO | WO 99 34796 A | 7/1999 |
| WO | WO 99 50265 A | 10/1999 |
| WO | WO 99 50266 A | 10/1999 |
| WO | WO 00 06541 | 2/2000 |
| WO | WO 00 06542 | 2/2000 |
| WO | WO 01 40181 A | 6/2001 |
| WO | WO 01 85144 | 11/2001 |

OTHER PUBLICATIONS

D'Alessio, Roberto et al: "Structure-activity relationship of novel distamycin A derivatives: Synthesis and antitumor activity" Bioorg. Med. Chem. Lett. (1994), 4(12), 1467-72, XP000671766.

Colella, G. et al: "Mismatch repair deficiency is associated with resistance to DNA minor groove alkylating agents" Br. J. Cancer (1999), 80(3/4), 338-343, XP001039733.

Giusti Anna Maria et al: "In vivo induction of apoptosis with PNU-166196 in human ovarian carcinoma xenogratfs." Proceedings of the American Association for Cancer Research Annual, No. 41, Mar. 2000, p. 825 XP001039865 91st Annual Meeting of the American Association for Cancer Research.: San Francisco, California, USA; Apr. 1-5, 2000, Mar., 2000 ISSN: 0197-016X.

Geroni Cristina et al: "Antitumor activity of PNU-166196, a novel DNA minor groove binder selected for clinical development." Proceedings of the American Association for Cancer Research Annual, No. 41, Mar. 2000, pp. 425-426, XP001039861 91st Annual Meeting of the American Association for Cancer Research.: San 2000, Mar., 2000 ISSN: 0197-016X.

Baraldi, Pier Giovanni et al: "Synthesis and antitumor activity of novel distamycin derivatives" Bioorg. Med. Chem. Lett. (1996), 6(11), 1241-1246 XP004134862 p. 1241, paragraph 2 example SCHEME1 p. 1244, paragraph 1 table 1 p. 1244, paragraph 4—p. 1245, paragraph 1.

(Continued)

*Primary Examiner*—Jeffrey Edwin Russel
(74) *Attorney, Agent, or Firm*—Scully, Scott, Murphy & Presser

(57) ABSTRACT

Compounds which are α-halogenoacryloyl distamycin derivatives of formula (I) wherein $R_1$ is a bromine or chlorine atom; $R_2$ is a distamycin or distamycin-like framework as set forth in the specification; or a pharmaceutically acceptable salt thereof; are cytotoxic agents particularly effective in the treatment of tumors over expressing GSH/GSTs system and which are poorly responsive or even resistant to conventional antitumor therapies.

16 Claims, No Drawings

OTHER PUBLICATIONS

Stewart D J et al: "Non-Chemotherapeutic Agents that Potentiate Chemotherapy Efficacy" Cancer Treatment Reviews, vol. 16, No. 1, 1989, pp. 1-40, XP001039737 ISSN: 0305-7372 p. 18, paragraph 3—p. 19, paragraph 1.

Tsuchida S et al: "Elevation of the Placental Glutathione-S-Transferase Form GST-PI in Tumor Tissues and the Levels in Sera of Patients with Cancer" Cancer Research, vol. 49, No. 18, 1989, pp. 5225-5229, XP001039783 ISSN: 0008-5472 abstract p. 5225, col. 1, paragraph 1 p. 5228, col. 1, paragraph 1 p. 5228, col. 2, paragraph 2.

Cozzi P: "A new class of cytotoxic DNA minor groove binders: alpha-halogenoacrylic derivatives of pyrrolecarbamoyl oligomers." FARMACO, (Jan.-Feb. 2001) 56 (1-2) 57-65., XP001039805 abstract p. 58, col. 2, paragraph 4 p. 59, col. 1, paragraph 1 figure 5 p. 60, col. 1, paragraph 2—p. 61, col. 1, paragraph 4 tables 2,3 p. 62, col. 2, paragraph 3 figures 9, 10 table 5 p. 63, col. 1, paragraph 1—col. 2, paragraph 2.

Geroni C et al: "PNU-166196: A novel antitumor agent whose cytotoxicity is enhanced in tumor cells with high levels of glutathione." Tumori, vol. 86, No. 4 Suppl. 1, Jul. 2000, pp. 41-42, XP001039871 XV Congress of the Italian Cancer Society; Turin, Italy; Oct. 5-7, 2000 ISSN: 0300-8916.

Cozzi, Paolo et al: "Cytotoxic.alpha.—bromoacrylic derivatives of distamycin analogs modified at the amidino moiety" Bioorg. Med. Chem. Lett. (2000), 10(11), 1273-1276, Jun. 2000, XP004200573 abstract p. 1273, col. 1, paragraph 3—col. 2, paragraph 1 table 1 p. 1274, col. 2, paragraph 3—paragraph 4 p. 1275, col. 1, paragraph 3—col. 2, paragraph 2.

Baraldi, Pier Giovanni et al: "Synthesis and Antitumor Activity of New Benzoheterocyclic Derivatives of Distamycin A" J. Med. Chem. (2000), 43(14), 2675-2684, Jul. 13, 2000, XP001039581 abstract p. 2676, col. 1; tables p. 2676, col. 1, paragraph 1 tables 1, 2 p. 2678, col. 2, paragraph 5—p. 2679, col. 1, paragraph 1 p. 2680, col. 2, paragraph 3.

Sola F et al: "The antitumor efficacy of cytotoxic drugs is potentiated by growth-factor-complexing molecule" Cancer Chemotherapy and Pharmacology, vol. 43, No. 3, 1999, pp. 241-246, XP002104215. ISSN: 0344-5704.

Zou J P et al: "Distamycin A derivatives potentiate tumor-necrosis factor activity via the modulation of tyrosine phosphorylation" International Journal Fo Cance, New York, NY, US, vol. 72, No. 5, 1997, pp. 810-814, XP002104217 ISSN: 0020-7136.

Tagliabue G et al: "Combination of the New Minor Groove Alkylator Tallimustine and Melphalan" European Journal of Cancer, Pergamon Press, Oxford, GB, vol. 33, No. 2, Feb. 1997, pp. 284-287, XP004282511 ISSN: 0959-8049.

Boger et al., "Total Synthesis of Distamycin A and 2640 Analogues: A Solution-Phase Combinatorial Approach to the Discovery of New Bioactive DNA Binding Agents and Development of a Rapid, High-Throughput Screen for Determining Relative DNA Binding Affinity or DNA Binding Sequence Selectivity", J. Am. Chem. Soc. 2000. 122. 6382-6394.

Cozzi P et al: "Cytotoxic halogenoacrylic derivatives of distamycin A" Bioorganic & Medicinal Chemistry Letters, oxford, GB, vol. 10, No. 11, Jun. 2000 (200-06), pp. 1269-1272, XP004200572 ISSN: 0960-894X.

Mosconi A M et al: XP004282426 "Combination Therapy with Gemcitabine in Non-Small Cell Lung Cancer" European Journal of Cancer, Pergamon Press, Oxford, GB, vol. 33, Jan. 1997, pp. S14-S17, ISSN: 0959-8049.

Catharina J A Van Moorsel et al: XP002110339 "Gemcitabine: Futrue Prospects of Single-Agent and Combination Studies" Oncologist, Alphamed Press, US, vol. 2, No. 3, 1997, pp. 127-134, ISSN: 1083-7159.

Budavari S (ED): XP002191966 "The Merck Index (12th Edition)" Merck Index, Encyclopedia of Chemicals, Drugs, and Biologicals, 13th. Edition 1996, Whitehouse Station, Merck & Co, US, vol. ED. 13, 2001, p. 4206 ISBN: 0-911910-12-3.

USE OF SUBSTITUTED ACRYLOYL DISTAMYCIN DERIVATIVES IN THE TREATMENT OF TUMORS ASSOCIATED WITH HIGH LEVELS OF GLUTATHIONE

The present invention relates to the use of substituted acryloyl distamycin derivatives, in particular to the use of α-bromo- and α-chloroacryloyl distamycin derivatives, in the treatment of tumors associated with high levels of glutathione and/or glutathione-S-transferases family.

More specifically, the present invention concerns the treatment of a human being diagnosed with a tumor over expressing glutathione/glutathione-S-transferases family, hereinafter solely referred to as GSH/GSTs, with the above acryloyl distamycin derivatives.

GSH plays a crucial protective role against cellular injury produced by a number of toxic insults. Preclinical and clinical studies have established a correlation between GSH/GSTs over expression and cancer or cancer response-rate to chemotherapy.

Alterations of the GSH-based detoxification system (consisting of GSH and GSH related enzymes, GSTs) have been also associated with varying responsiveness to several antineoplastic agents.

Both GSH and GSTs are ubiquitously present in several human tissues such as, for instance, blood cells, plasma, serum, circulating blasts and pathologic (tumor) tissues.

See, for a general reference to GSH and GSTs, *Cancer Res.* 54:4313–4320 (1994); *Brit. J. Cancer* 72(2): 324–326 (1995); *DDT* 3:113–121 (1998).

GSTs, and most prominently GST-π, are present at high levels in a preponderance of tumor types. Increased activity of GSH/GSTs in comparison to normal tissues has been found in several tumor tissues comprising, for instance, gastrointestinal tumors (including esophageal, gastric, colon, hepatocellular and pancreatic), uterine and ovarian cancers, head and neck cancer, lung and NSCL carcinomas as well as metastatic liver tumors originating from the colon, stomach and bladder [*Cancer Res.* 49:5225–5229 (1989); *Clinical Reviews in Biochemistry and Molecular Biology* 27(4.5):337–386 (1992)].

To establish the role of GSH/GSTs towards inactivity and/or resistance of tumor cells to cytotoxic drugs, two major experimental approaches have been followed.

The first of them involved studies in which elevated levels or expression and activity of GSH/GSTs were correlated with increased levels of drug resistance. This approach also included modulation of GSH/GSTs activity by means of GSH inhibitors such as BSO (buthionine sulphoximine), in order to circumvent or reverse drug resistance.

The second approach, used in transfection studies, provided direct functional evidence that GSH/GSTs caused drug resistance.

Evidence exists that GSH/GSTs play a major role in resistance to alkylating agents (e.g. melphalan, chlorambucil, cyclophosphamide, ifosfamide mustards, BCNU) and platinum complexes such as cisplatin, carboplatin and oxaliplatin [*Biochem. Pharmacol* 35: 3405–3409 (1986)]. Recently, the role of GSH in drug resistance has been linked to the regulation of the activity of the multi-drug resistance-associated proteins (MRP) which confer resistance to different cytotoxics including anthracyclines (e.g. doxorubicin, idarubicin, epirubicin and derivatives thereof), epidophyllotoxins (e.g. etoposide and teniposide), vinca alkaloids (e.g. vinblastine and vincristine) and taxanes (e.g. paclitaxel and docetaxel) [*Eur. J. Cancer* 32: 945–957 (1996); *Seminars in Oncol.* 24(5):580–591, (1997)].

It has now been found that, unlike other well known cytotoxic distamycin derivatives, those bearing an α-bromo- or α-chloroacryloyl moiety, as set forth below according to the object of the present invention, are surprisingly effective in the treatment of tumors over expressing GSH/GSTs system, hence known to be poorly responsive to conventional antitumor therapies and/or to cause resistance once therapeutic cytotoxic agents are administered.

Distamycin A and analogs thereof, hereinafter referred to as distamycin and distamycin-like derivatives, are known in the art as cytotoxic agents useful in antitumor therapy.

Distamycin A is an antibiotic substance with antiviral and antiprotozoal activity, having a polypyrrole framework [*Nature* 203: 1064 (1964); *J. Med. Chem.* 32: 774–778 (1989)].

The international patent applications WO 90/11277, WO 98/04524, WO 98/21202, WO 99/50265, WO 99/50266 as well as the co-pending still unpublished International patent application No. PCT/EP00/11714 (filed on 23 Nov. 2000 and claiming priority from British patent application 9928703.9), all in the name of the applicant itself and herewith incorporated by reference, disclose acryloyl distamycin derivatives wherein the amidino moiety of distamycin is optionally replaced by nitrogen-containing ending groups such as, for instance, cyanamidino, N-methylamidino, guanidino, carbamoyl, amidoxime, cyano and the like, and/or wherein the polypyrrole framework of distamycin, or part of it, is replaced by varying carbocyclic or heterocyclic moieties.

Therefore, a first object of the present invention is the use of a α-halogenoacryloyl distamycin derivative of formula (I)

wherein:
$R_1$ is a bromine or chlorine atom;
$R_2$ is a distamycin or distamycin-like framework;
or a pharmaceutically acceptable salt thereof;
in the manufacture of a medicament for the treatment of tumors over expressing GSH/GSTs system.

According to a preferred embodiment of the invention, the above compounds of formula (I) are useful for treating tumors over expressing GSH/GSTs system and comprising gastrointestinal tumors, including esophageal, gastric, colon, hepatocellular and pancreatic tumor, uterine and ovarian cancers, head and neck cancer, lung and NSCL carcinomas as well as metastatic liver tumors originating from the gastrointestinal, uterine, ovarian and lung cancers.

A further embodiment of the invention is the use of the compounds of formula (I) in the treatment of tumors which over express GSH/GSTs system as a result of a previous chemotherapy treatment, for example a first-line chemotherapy treatment with alkylating agents, platinum derivatives or anthracyclines.

More specifically, the previous chemotherapy treatment may comprise alkylating agents, for instance melphalan, chlorambucil, cyclophosphamide, ifosfamide mustards and BCNU; platinum complexes, for instance cisplatin, carboplatin and oxaliplatin; anthracyclines, for instance doxorubicin, idarubicin, epirubicin and derivatives thereof; epidophyllotoxins, for instance etoposide and teniposide; vinca alkaloids, for instance vinblastine and vincristine; taxanes, for instance paclitaxel and docetaxel.

The present invention includes within its scope the use of all the possible isomers covered by the compounds of formula (I), both considered separately or in admixture, as well as the metabolites and the pharmaceutically acceptable bio-precursors (otherwise known as pro-drugs) of the compounds of formula (I).

Within the compounds of formula (I), unless otherwise specified, with the term distamycin or distamycin-like framework $R_2$ we intend any moiety structurally closely related to distamycin itself, for instance by replacing the ending amidino moiety of distamycin and/or its polypyrrole framework, or part of it.

A preferred embodiment of the invention provides the use of the compounds of formula (I), as above indicated, wherein $R_1$ has the above reported meanings and $R_2$ is a group of formula (II) below:

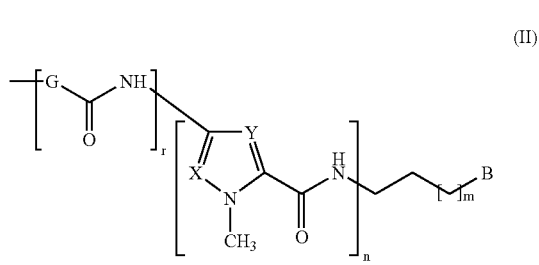

(II)

wherein
m is an integer from 0 to 2;
n is an integer from 2 to 5;
r is 0 or 1;
X and Y are, the same or different and independently for each heterocyclic ring, a nitrogen atom or a CH group;
G is phenylene, a 5 or 6 membered saturated or unsaturated heterocyclic ring with from 1 to 3 heteroatoms selected among N, O or S, or it is a group of formula (III) below:

(III)

wherein Q is a nitrogen atom or a CH group and W is an oxygen or sulfur atom or is a group $NR_3$ wherein $R_3$ is hydrogen or $C_1$–$C_4$ alkyl;
B is selected from the group consisting of

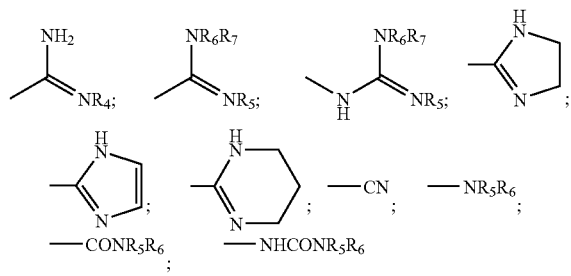

wherein $R_4$ is cyano, amino, hydroxy or $C_1$–$C_4$ alkoxy; $R_5$, $R_6$ and $R_7$, the same or different, are hydrogen or $C_1$–$C_4$ alkyl.

In the present description, unless otherwise specified, with the term $C_1$–$C_4$ alkyl or alkoxy group we intend a straight or branched group selected from methyl, ethyl, n-propyl, isopropyl, n-butyl, isobutyl, sec-butyl, tert-butyl, methoxy, ethoxy, n-propoxy, isopropoxy, n-butoxy, isobutoxy, secbutoxy or tert-butoxy.

A more preferred embodiment of the invention provides the use of the above compounds of formula (I) wherein $R_1$ is bromine or chlorine; $R_2$ is the above group of formula (II) wherein r is 0, m is 0 or 1, n is 4 and B has the above reported meanings.

Still more preferred is the use of the compounds of formula (I) wherein $R_1$ is bromine or chlorine; $R_2$ is the above group of formula (II) wherein r is 0, m is 0 or 1, n is 4, X and Y are both CH groups and B is selected from:

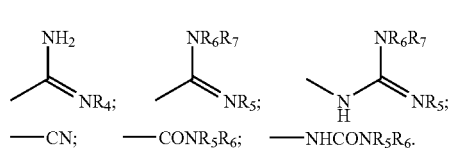

where in $R_4$ is cyano or hydroxy and $R_5$, $R_6$ and $R_7$, the same or different, are hydrogen or $C_1$–$C_4$ alkyl.

Pharmaceutically acceptable salts of the compounds of formula (I) are those with pharmaceutically acceptable inorganic or organic acids such as, for instance, hydrochloric, hydrobromic, sulfuric, nitric, acetic, propionic, succinic, malonic, citric, tartaric, methanesulfonic, p-toluenesulfonic acid and the like.

Examples of preferred compounds of formula (I) in the manufacture of a medicament for the treatment of tumors over expressing GSH/GSTs system, optionally in the form of pharmaceutically acceptable salts, preferably with hydrochloric acid, are:

1. N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3yl)-4-[(2-bromoacryloyl)amino]-1-methyl-1H -pyrrole-2-carboxamide hydrochloride;

2. N-(5-{[(5-{[(5-{[(2-{[amino(imino)methyl]amino}propyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride;

3. N-(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride;

4. N-(5-{[(5-{[(5-{[(3-amino-3-iminopropyl)amino]carbonyl}-1-methyl-1H -pyrrol-3-yl)amino]carbonyl}-1-methyl-1H-pyrrol-3-yl)amino]carbonyl}-1-methyl-1H -pyrrol-3-yl)-4-[(2-bromoacryloyl)amino]-1-methyl-1H-imidazole-2-carboxamide hydrochloride;

5. N-(5-{[(5-{[(5-{[(3-amino-3-iminopropyl)amino]carbonyl}-1-methyl-1H -pyrrol-3-yl)amino]carbonyl}-1-methyl-1H-pyrrol-3-yl)amino]carbonyl}-1-methyl-1H -pyrrol-3-yl)-3-[(2-bromoacryloyl)amino]-1methyl-1H-pyrazole-5-carboxamide hydrochloride;

6. N-(5-{[(5-{[(5-{[(3-amino-3-oxopropyl)amino]carbonyl}-1-methyl-1H -pyrrol-3-yl)amino]carbonyl}-1-methyl-1H-pyrrol-3-yl)amino]carbonyl}-1-methyl-1H-pyrrol-3-yl)-3-[(2-bromoacryloyl)amino]-1-methyl-1H-pyrazole-5-carboxamide;
7. N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)4-[(2-chloroacryloyl)amino]-1-methyl-1H-pyrrol-2-carboxamide hydrochloride;
8. N-(5-{[(5-{[(3-{[amino(imino)methyl]amino}propyl)amino]carbonyl}-1-methyl -1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride;
9. N-(5-{[(5-{[(3-amino-3-iminopropyl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride; and
10. N-{5-[({5-[({5-[({3-[(aminocarbonyl)amino]propyl}amino)carbonyl]-1-methyl-1H-pyrrol-3-yl}amino)carbonyl]-1-methyl-1H-pyrrol-3-yl}amino)carbonyl]-1-methyl-1H-pyrrol-3-yl}-4-[(2-bromoacryloyl)amino]-1-methyl-1H-pyrrol-2-carboxamide.

The above compounds of formula (I), either specifically identified as such or by means of the general formula, are known or easily prepared according to known methods as reported, for instance, in the aforementioned international patent applications WO 90/11277, WO 98/04524, WO 98/21202, WO 99/50265 and WO 99/50266 as well as in the co-pending International patent application No. PCT/EP00/11714.

Pharmacology

The compounds of formula (I), according to the present invention, are highly effective in the treatment of tumors associated with high levels of GSH/GSTs and find application in the treatment of several tumors which are scarcely responsive or even not susceptible to conventional chemotherapeutic agents.

The role of GSH on the cytotoxic activity of the compounds of formula (I) has been investigated by testing the compounds on a chemoresistant tumor cell subline presenting levels of GSH/GSTs higher than those of the parental cell line. The used model is a melphalan (L-PAM) resistant murine leukemia (L1210/L-PAM) which presents a three fold increased amount of GSH (25.8 nmole/$10^6$ cells) with respect to the normal L1210 (7.7 nmole/$10^6$ cells) cell line (Table I).

The tested compounds of formula (I) are:
N-(5-{[(5-{[(5-{[(2-{[amino(imino)methyl]amino}ethyl)amino]carbonyl}-1-methyl-1H-pyrrpl-3-yl)amino]carbonyl}-1-methyl-1H-pyrrol-3-yl)amino]carbonyl}-1-methyl-1H-pyrrol-3-yl)-4-[(2-bromoacryloy)amino]-1-methyl-1H-pyrrol-2-carboxamide hydrochloride—internal code PNU 166196; and
N-(5-{[(5-{[(5-{[(3-amino-3-iminopropyl)amino]carbonyl}-1-methyl-1H-pyrrol -3-yl)amino]carbonyl}-1-methyl-1H-pyrrol-3-yl)amino]carbonyl}-1-methyl-1H -pyrrol-3-yl)-4-[(2-bromoacryloyl)amino]-1-methyl-1H-pyrrole-2-carboxamide hydrochloride—internal code PNU 151807.

The distamycin derivative 3-[1-methyl-4-[1-methyl-4-[1-methyl-4-[1-methyl-4-[N,N-bis(2-chloroethyl)amino]benzenecarboxamido]pyrrole-2-carboxamido]pyrrole-2-carboxamido]pyrrole-2-carboxamido]propionamidine, better known as tallimustine, and L-PAM were tested as controls in the same experimental conditions.

Data, reported in Table I, clearly indicate that the cytotoxicity of the compounds of formula (I) was increased on L1210/L-PAM cells by three fold in respect to L1210 cells (PNU 166196=$IC_{50}$ 0.49 and 1.62 ng/ml, respectively; PNU 151807=$IC_{50}$ 0.26 and 0.86 ng/ml, respectively). The cytotoxicity of tallimustine was comparable on the two cell lines; conversely the cytotoxicity of L-PAM was lower on L1210/L-PAM cells than on L1210 cells.

TABLE I

| Cell line | GSH (nmole/$10^6$ cells) | Cytotoxicity[a] $IC_{50}$ (ng/ml) | | | |
|---|---|---|---|---|---|
| | | PNU 166196 | PNU 151807 | Tallimustine | L-PAM |
| L1210 | 7.7 | 1.62 | 0.86 | 22.5 | 1650 |
| L1210/L-PAM | 25.8 | 0.49 | 0.26 | 27.4 | 8100 |

[a]Cells incubated with the compound for 48 h. Growth Inhibition determined by counting surviving cells.

Further evidence of the relevance of GSH levels for the cytotoxicity of the compounds of formula (I) has been obtained by determining the influence of prior treatment with BSO (L-S.R buthionine sulphoximine) on the susceptibility of A2780 human ovarian cells to their cytotoxic and apoptotic effect.

BSO is a potent and specific inhibitor of γ-glutamylcysteine synthetase, the rate-limiting step in GSH biosynthesis. Depletion of intracellular GSH by BSO significantly enhances the cytotoxicity of many antitumor drugs, principally alkylating agents such as melphalan and chlorambucil and platinum compounds such as cisplatin, carboplatin and oxaliplatin [*Chemico-Biological Interactions* 111:239–254 (1998)].

As shown in Table II, the cytotoxicity (percentage of growth inhibition) and the apoptotic effect (percentage of cells with apoptotic morphology) of PNU 166196, as a representative compound of formula (I), were significantly decreased in A2780 cells pretreated with BSO in respect to the BSO-untreated ones.

TABLE II

| Treatment[a] | Dose | Growth inhibition % | Apoptosis % |
|---|---|---|---|
| PNU 166196 | 300 (ng/ml) | 43 ± 2.5 | 17.5 ± 6.5 |
| | 1000 (ng/ml) | 64.5 ± 14.5 | 49.5 ± 15.5 |
| | 3000 (ng/ml) | 77.5 ± 6.5 | 74.5 ± 15.5 |
| PNU 166196 + | 300 (ng/ml) | 31.5 ± 2.5 | 1.5 ± 0.5 |
| BSO 0.1 mM | 1000 (ng/ml) | 33 ± 11 | 5.5 ± 2.5 |
| | 3000 (ng/ml) | 38 ± 7 | 11.5 ± 5.5 |
| BSO[b] | MM | 2.5 ± 0.2 | 0 |

[a]Cells incubated with the compound for 48 h. Growth inhibition was determined by counting surviving cells and apoptosis was evaluated by morphological examination.
[b]Cells exposed to BSO for 24 h before and during PNU 166196 treatment.

PNU 166196 showed a decreased cytotoxicity in A2780 cells pretreated with BSO in respect to the untreated cells (38 and 77.5% growth inhibition at 3000 ng/ml, respectively). The decreased potency of PNU 166196 in tumor cells pretreated with BSO was also confirmed by testing the percentage of cells with apoptotic morphology +/− BSO (11.5 and 74.5% at 3000 ng/ml, respectively).

The above results support the evidence that the in vitro activity of α-bromo- and α-chloroacryloyl distimycin derivatives of formula (I) is greatly affected by the presence of high levels of GSH and, consequently, these compounds are particularly useful in the treatment of tumors over expressing GSH/GSTs.

The compounds of the invention can be administered by the usual routes, for example, parenterally, e.g. by intravenous injection or infusion, intramuscularly, subcutaneously, topically or orally.

The dosage depends on the age, weight and conditions of the patient and on the administration route. For example, a suitable dosage for administration to adult humans may range from about 0.05 to about 100 mg pro dose from 1 to 4 times a day.

The pharmaceutical compositions may contain an effective amount of a compound of formula (I), as the active substance, in association with one or more pharmaceutically acceptable excipients and are usually prepared following conventional methods.

For instance, solutions for intravenous injection or infusion may contain sterile water as a carrier or, preferably, they may be in the form of sterile aqueous isotonic saline solutions.

Suspensions or solutions for intramuscular injections may contain, together with the active compound, a pharmaceutically acceptable carrier, e.g. sterile water, olive oil, ethyl oleate, glycols, e.g. propylene glycol and, if desired, a suitable amount of lidocaine hydrochloride. In the form for topical application, e.g. creams, lotions or pastes for use in dermatological treatment, the active ingredient may be mixed with conventional oleaginous or emulsifying excipients.

The solid oral forms, e.g. tablets and capsules, may contain, together with the active compound, diluents, e.g. lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl-cellulose, polyvinylpyrrolidone; disaggregating agents, e.g. a starch, alginic acid, alginates, sodium starch glycolate; effervescing mixtures; dyestuffs; sweeteners; wetting agents, for instance, lecithin, polysorbates, laurylsulphates; and, in general, non-toxic and pharmacologically inactive substances used in pharmaceutical formulations. Said pharmaceutical preparations may be manufactured in a known manner, for example by means of mixing, granulating, tabletting, sugar-coating, or film-coating processes.

Furthermore, according to the present invention, there is provided a method of treating tumors over expressing GSH/GSTs system in a patient in need of it which comprises administering to the said patient a composition of the invention.

The following examples are herewith intended to better illustrate the present invention without posing any limitation to it.

EXAMPLE 1

Cytotoxic Activity of the Compounds of Formula (I) Against Tumors Associated with High Levels of GSH The compounds N-(5-{[(5-{[(5-{[(2-{[amino(imino)methyl]amino}ethyl)amino] carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl) amino]-1-methyl-1H-pyrrole -2-carboxamide hydrochloride (PNU 166196) and N-(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride (PNU 151807), respectively prepared as described in WO 98/04254 and WO 90/11277, were dissolved in sterile water and immediately used for the experiments.

The cytotoxic activity was determined on L1210 murine lymphocytic leukemia cell line and on the L-PAM resistant cell subline L1210/L-PAM. Cells were grown in vitro as stabilized suspension cultures. L1210 cells were maintained in RPMI 1640 medium containing β-mercaptoethanol (10 μM). L1210/L-PAM cells were maintained in RPMI 1640 medium containing β-mercaptoethanol (50 μM). All culture media (Biowhittaker, UK) were supplemented with 10% Fetal Calf Serum (Biological Industries, Israel) and 2 mM L-glutamine (Biowhittaker, UK).

The cytotoxic activity was determined against exponentially growing cells. L1210 and L1210/L-PAM cells were seeded in 24 well-plates at concentration of 50,000 cells/ml and immediately treated for 48 h with the drug.

The inhibition of cell growth was evaluated by counting surviving cells with a Coulter Counter. The antiproliferative activity of drugs was calculated from dose-response curves and expressed as $IC_{50}$ (concentration inhibiting 50% cell growth in treated cultures relative to untreated controls). All the experiments were carried out twice.

Results are reported per the enclosed table I and comments thereof.

EXAMPLE 2

Cytotoxicity and Apoptotic Effect of PNU 166196 on A2780 Cells Pretreated with BSO The compound PNU 166196 (see example 1 above) was dissolved in sterile water and immediately used for the experiments. BSO was dissolved in sterile water and filtered with a 0.2μ filter.

The cytotoxic activity was determined on A2780 human ovarian carcinoma cell line. Cells were grown in vitro as monolayer cultures in RPMI 1640 medium (Biowhittaker, UK) supplemented with 10% Fetal Calf Serum (Biological Industries, Israel) and 2 mM L-glutamine (Biowhittaker, UK).

The cytotoxic activity was determined against exponentially growing cells. A2780 cells were seeded in 6 well-plates at concentration of 100,000 cells/ml for 2 ml and incubated for 24 h with the GSH inhibitor BSO and finally exposed to different concentrations of PNU 166196 (untreated cells were incubated with the medium only).

After 24 h treatment with the drug, cell growth inhibition was evaluated on the monolayer cells whereas the floating cells were used for morphology evaluation.

Apoptosis was evaluated by fluorescence microscopy. At the end of the treatment, floating cells were collected, washed in PBS, fixed in 70% ice-cold ethanol and stored at −20° C. until analysis (5 days max.). Cells were then centrifuged and the pellets were stained with 50 μg/ml propidium iodide, 0.001% Nonidet P40 and 60 U/ml Rnase and stored in the dark for 30 minutes at 37° C. Cells were centrifuged and the pellets were resuspended in 50 μM PBS. At least 600 cells randomly chosen from 2 smears independently prepared were examined for their nuclear morphology changes (chromatin condensation and DNA fragmentation) using a fluorescence microscope [see *Int. J. Cancer*

65:491–497 (1996)]. All the experiments were carried out twice. Results are reported per the enclosed table II and comments thereof.

What is claimed is:

1. A method for the treatment of tumors in humans overexpressing GSH/GSTs comprising administering to said human an α-halogenoacryloyl distamycin derivative of formula (I)

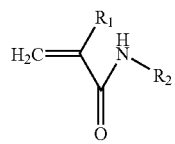

wherein:
$R_1$ is a bromine or chlorine atom; and
$R_2$ is a distamycin or distamycin-like framework; or an acceptable salt thereof.

2. The method according to claim 1 wherein the tumor overexpressing GSH/GSTs is a gastrointestinal tumors.

3. The method according to claim 1 wherein the overexpression of GSH/GSTs is the result of a previous first-line chemotherapy treatment with a cytotoxic agent.

4. The method according to claim 3 wherein the cytotoxic agent is selected from alkylating agents, platinum complexes, anthracyclines, epidophyllotoxins, vinca alkaloids, and taxanes.

5. The method according to claim 1 wherein, in the α-halogenoacryloyl distamycin derivative of formula (I), $R_2$ is a group of formula (II):

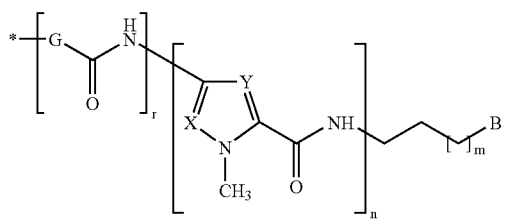

wherein
m is an integer from 0 to 2;
n is an integer from 2 to 5;
r is 0 or 1;
X and Y are, the same or different and independently for each heterocyclic ring, a nitrogen atom or a CH group;
G is phenylene, a 5 or 6 membered saturated or unsaturated heterocyclic ring with from 1 to 3 heteroatoms selected among N, O or S, or it is a group of formula (III) below:

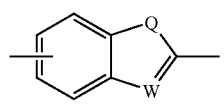

wherein Q is a nitrogen atom or a CH group and W is an oxygen or sulfur atom or is a group $NR_3$ wherein $R_3$ is hydrogen or $C_1$–$C_4$ alkyl;

B is selected from the group consisting of

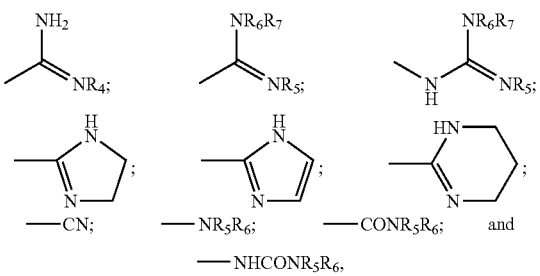

—CN;  —NR$_5$R$_6$;  —CONR$_5$R$_6$;  and
—NHCONR$_5$R$_6$, wherein $R_4$ is cyano, amino, hydroxy or $C_1$–$C_4$ alkoxy;
$R_5$, $R_6$ and $R_7$, the same or different, are hydrogen or $C_1$–$C_4$ alkyl.

6. The method according to claim 5 wherein, in the α-halogenoacryloyl distamycin derivative of formula (I), $R_1$ is bromine or chlorine; and $R_2$ is a group of formula (II) wherein r is 0, m is 0 or 1, n is 4 and B is as defined in claim 5.

7. The method according to claim 6 wherein, in the α-halogenoacryloyl distamycin derivative of formula (I), $R_1$ is bromine or chlorine; $R_2$ is a group of formula (II):

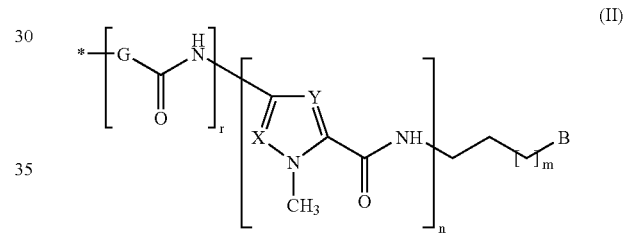

wherein
m is an integer from 0 to 1;
n is 4;
r is 0;
X and Y are CH groups;
G is phenylene, a 5 or 6 membered saturated or unsaturated heterocyclic ring with from 1 to 3 heteroatoms selected among N, O or S, or it is a group of formula (III) below:

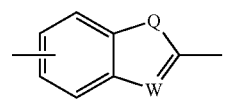

wherein Q is a nitrogen atom or a CH group and W is an oxygen or sulfur atom or is a group $NR_3$ wherein R3 is hydrogen or $C_1$–$C_4$ alkyl;

B is selected from the group consisting of

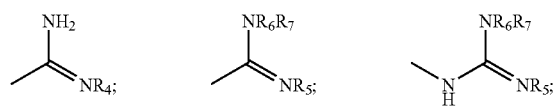

—CN; —CONR₅R₆; —NHCONR₅R₆ wherein R₄ is cyano or hydroxy and R₅, R₆ and R₇, the same or different, are hydrogen or $C_1$–$C_4$ alkyl.

8. The method according to claim 1 wherein the α-halogenoacryloyl distamycin derivative of formula (I), optionally in the form of a pharmaceutically acceptable salt, is selected from:

1. N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-methyl-1H-pyrrol-3-yl)-4-[(2-bromoacryloyl)amino]-1-methyl-1H-pyrrole-2-carboxamide;
2. N-(5-{[(5-{[(5-{[(2-{[amino(imino)methyl]amino}propyl)amino]carbonyl }-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide;
3. N-(5-{[(5-{[(5-{[(3-amino-3-iminopropyl-)amino]carbonyl}-1-methyl-1H-pyrrol-3-yl)amino]carbonyl}-1-methyl-1H-pyrro-3-yl)amino]carbonyl}-1-methyl-1H-pyrrol-3-yl)-4-[(2-bromoacryloyl)amino]-1-methyl-1H-pyrrole-2-carboxamide;
4. N-(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-imidazole-2-carboxamide;
5. N-(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-3-[(2-bromoacryloyl)amino]-1-methyl-1H-pyrazole-5-carboxamide;
6. N-(5-{[(5-{[(5-{[(3-amino-3-oxopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-3-[(2-bromoacryloyi)amino]-1-methyl-1H-pyrazole-5-carboxamide;
7. N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl-1-methyl-1H-pyrrol-3-yl)-4-[(2-chloroacryloyl)amino]-1-methyl-1H-pyrrole-2-carboxamide;
8. N-(5-{[(5-{[(3-{[amino(imino)methyl]amino}propyl)amino]-carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide;
9. N-(5-{[(5-{[(3-amino-3-iminopropyl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide; and
10. N-{5-[({5-[({5-[({3-[(aminocarbonyl)amino]propyl}amino)carbonyl]-1-methyl-1H-pyrrol-3-yl}amino)carbonyl]-1-methyl-1H-pyrrol-3-yl}amino)carbonyl]-1-methyl-1H-pyrrol-3-yl}-4-[(2-bromoacryloyl)amino]-1-methyl-1H-pyrrole-2-carboxamide.

9. The method according to claim 8 wherein the α-halogenoacryloyl-distamycin derivative of formula (I) is N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride.

10. The method according to claim 1 wherein said tumors are selected from the group consisting of esophageal, gastric, colon, hepatocellular and pancreatic tumor, uterine and ovarian cancers, head and neck cancer, lung and NSCL carcinomas and metastatic liver tumors originating from the gastrointestinal, uterine, ovarian and lung cancers.

11. The method according to claim 4, wherein said alkylating agents are selected from the group consisting of melphalan, chlorambucil, cyclophosphamide, ifosfamide mustards and BCNU.

12. The method according to claim 4, wherein said platinum complexes are selected from the group consisting of cisplatin, carboplatin and oxaliplatin.

13. The method according to claim 4, wherein said anthracyclines are selected from the group consisting of doxorubicin, idarubicin, epirubicin and derivatives thereof.

14. The method according to claim 4, wherein said epidophyllotoxins are selected from the group consisting of etoposide and teniposide.

15. The method according to claim 4, wherein said vinca alkaloids are selected from the group consisting of vinblastine and vincristine.

16. The method according to claim 4, wherein said taxanes are selected from the group consisting of paclitaxel and docetaxel.

* * * * *